United States Patent [19]
Rubens

[11] 4,021,915
[45] May 10, 1977

[54] PERMANENT COLORING COAT FOR NATURAL TEETH

[76] Inventor: Harry Ernest Rubens, 14 Brookside Court, East Brunswick, N.J. 08816

[22] Filed: Aug. 13, 1974

[21] Appl. No.: 488,527

[52] U.S. Cl. ............................................. 32/15
[51] Int. Cl.² ...................................... A61K 5/02
[58] Field of Search ................... 32/1, 12, 15, 8; 106/35; 427/180, 421, 427

[56] References Cited
UNITED STATES PATENTS

| | | | |
|---|---|---|---|
| 1,779,850 | 10/1930 | Maurer | 32/15 |
| 2,000,285 | 5/1935 | Hoffmann | 106/6 |
| 3,250,002 | 5/1966 | Collito | 32/15 X |
| 3,413,723 | 12/1968 | Wagner et al. | 32/8 |
| 3,423,828 | 1/1969 | Halpern et al. | 32/8 |
| 3,518,762 | 7/1970 | Takeuchi | 32/15 |
| 3,663,501 | 5/1972 | Adams et al. | 32/15 X |
| 3,730,763 | 5/1973 | Schlottmann | 427/427 |
| 3,792,531 | 2/1974 | Rossi | 32/15 |
| 3,801,344 | 4/1974 | Dietz | 32/8 X |

*Primary Examiner*—Robert Peshock
*Attorney, Agent, or Firm*—Harry Ernest Rubens

[57] ABSTRACT

The method of changing the entire buccal surface area of a tooth, which comprises applying a layer of glue to the entire buccal area of the tooth and thereafter blowing powdered particles having the desired color, on the buccal surface, said glue being sufficiently tenacious to permanently lock said particles to the glue, and said particles having a hardness approaching that tooth enamel.

1 Claim, 3 Drawing Figures

PERMANENT COLORING COAT FOR NATURAL TEETH

My invention relates to a coating for natural teeth and more particularly to a layer of porcelain, quartz, or natural tooth enamel particles affixed to the front, or worn surfaces of natural teeth.

The injection of antibiotics or hormones into the body may in some instances cause a discoloration of the teeth which is permanent and therefor objectionable.

No method is known for restoring such teeth to a natural color except by applying a temporary coating of plastic which is not permanent and which tends to be quickly shed by the teeth.

It is a primary object of my invention to provide a permanent natural appearing coating to discolored or worn natural teeth, or teeth having visible metal inserts, to restore them to their original color and appearance.

I have found a method which comprises the use of porcelain, quartz, or natural tooth enamel taken from extracted teeth, grinding the same into small particle size and applying the same in adhering layers to produce the necessary opacity for eliminating the discoloration, coloring particles to provide a natural color background and translucent or transparent particles to restore the teeth to their natural and original color and translucency.

I accomplish these and other objects and obtain my new results as will be apparent from the coated tooth described in the following specification particularly pointed out in the claims and illustrated in the accompanying drawing in which:

I obtain the desired results with the use of a surgical glue such as the cyanoacrylates or variations thereof of which alpha cyanoacrylate is an example. Such a glue has been found by years of use to adhere surgically to slit tissue inside the body and form a permanent waterproof bond, especially useful when the tissue is incapable of supporting sutures. The glue is so adherent that one drop of the glue can cause the fingers to adhere so securely that surgery may be required to separate them.

In practice the mouth is provided with a rubber shield to expose only the tooth to be treated, thus insuring that the accidental splash of the glue will not engage any part of the mouth except the area of the tooth it is desired to coat.

Usually it is sufficient to just coat the front of the teeth and areas visible from the front.

Figure 1:
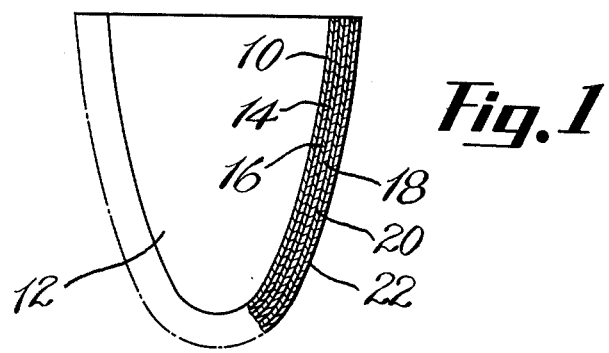
FIG. 1 is a cross-sectional view of an upper front tooth indicating the adhering layers that may be secured to the front surface of the tooth.
Figure 2:
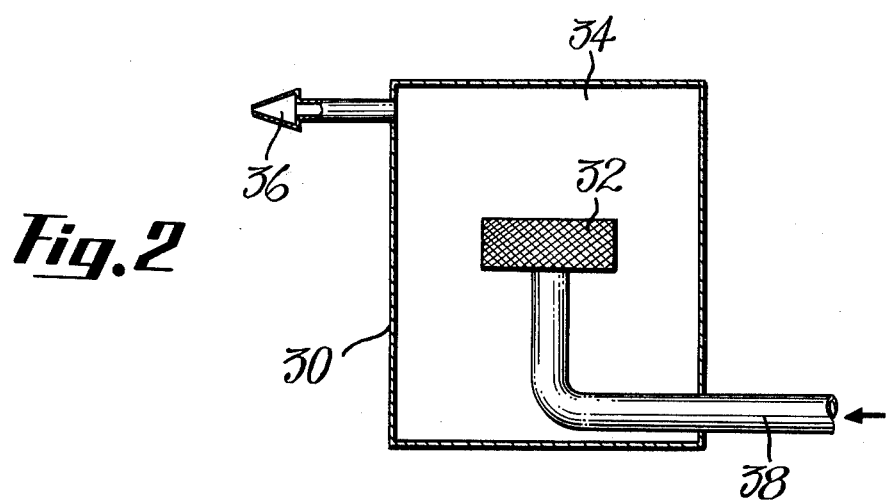
FIG. 2 is a schematic arrangement for applying a stream of powdered particles to the teeth.

In the drawing FIG. 1, the glue 10 is shown applied directly from its container to the tooth 12 until the desired area is coated. Then a powdered opaque material 14 may be applied to the coated areas until the discolored portion is hidden from view. It it is desired to hide a metal filling such as silver, it may be necessary to apply the glue again to the metal portion followed immediately by the powdered opaqueing material which may be titanium oxide, zirconium oxide or other known metal oxides which are white. Usually only a thin layer of the powder need be applied.

The opaqueing powder layer may be followed by another layer of glue 16 followed by a second layer of powdered porcelain particles 18 which have been colored to the desired color by metal oxides forming a pigment in the porcelain when heated therewith, and before powdering as is well known in the art of manufacturing artificial teeth.

A third layer of the glue 20 may be deposited followed by porcelain or quartz particles 22 which are translucent on the teeth.

The final coating need not be covered with the glue as the powdered particles are tenaciously held to the teeth so that they sometimes require a diamond studded dental burr for removal.

In fact such a burr may be used to remove uneven or excess material which may be the result of a failure to distribute the particles evenly on the glue.

I prefer to churn, the particles in a small chamber 30 by a disperser 32 until an even dispersion and separation of the particles occurs as at 34, which is followed by spraying the particles through nozzle 36 over the glue until an even distribution occurs. The spray is formed by air at high pressure entering the opening 38.

The spraying of the particles is similar to the spraying of finely dispersed, so called atomized paint particles which is used in spray picture painting.

The finer the particle size the finer the actual finish. A 5 micron size of particle has produced useful results.

After each coating of the powdered particles on the glue, the layer may be polished using gem polishing materials that can be washed away after polishing. Jewelers rouge is such a polishing medium. In the accidental event that a lower layer is exposed at any point the area may be reglued and repowdered, and if necessary repolished.

Instead of forming three layers of opaque colored and translucent particles successively, two layers may be used. Thus the opaque and coloring layers may be combined as a single powder.

Figure 3:
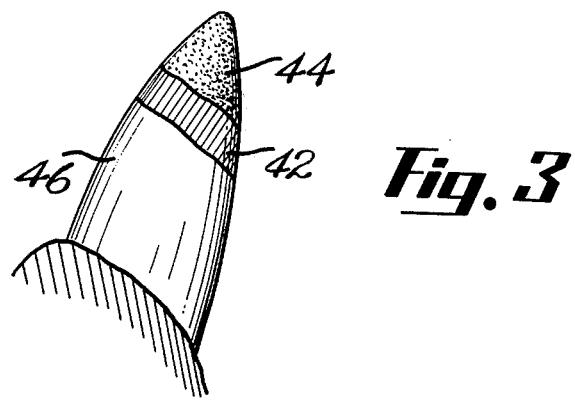
FIG. 3 is a cross-sectional view of a lower worn tooth indicating an area of erosion or wear at the biting edge which erosion or worn areas have been restored by a built up layer or layers of porcelain, quartz or enamel particles.

In some cases where the discoloration is minimal it may be possible to use a combined coloring and translucent powder particles to permit a single powdered layer on the glue.

Where worn or eroded areas are involved such as worn lower front teeth shown in FIG. 3, the glue 42 will support the particles 44 in the area of the teeth 46 without damage to exposed dentine. This may be required for building up the particle layers.

Medical report in;icate that after 6 years of glue adhering tissue within the body, no changes have occurred in the tissue which would warrant the belief that the glue is toxic or otherwise harmful to bone or tissue structure.

The glue is so resistant to being dislogded from the tooth surface that metal picks used for removing tartar from the teeth have been broken in an attempt to remove the glued porcelain particle layers.

Further, the glue will not disintegrate in the mouth fluids and it appears to be as useful in teeth restorations as it is in mending surgically parted tissues.

Since the glue instantly sets when it comes in contact with any particles, it cannot be used to provide a mixture of glue and particles as has been attempted hitherto in tooth coloring resins.

I have thus described my invention, but I desire it understood that it is not confined to the particular form or use shown and described, the same being merely illustrative, and that the invention may be carried out in other ways using equivalent instrumentalities without departing from the spirit of my invention.

What is claimed is:

1. A method of restoring a discolored surface of a natural tooth to its original color, which comprises applying a layer of glue to the entire buccal surface of the tooth, and applying to said glued surface immediately thereafter, by blowing, a thin layer of dry powdered colored particles, at ambient temperatures, having a thickness not substantially greater than the thickness of a single particle, forming an entirely new surface over the buccal area in the original color of the tooth, said glue characterized by being sufficient tenacious to adhere to both the tooth and the powdered particles and to resist removal except by wear of the powdered particles, resistant to mouth liquids, non-toxic, being a liquid when applied, whereby the glue will set immediately upon contact with the powdered particles, to limit the thickness of the layer of particles to a single particle thickness on the surface of the glue.

* * * * *